United States Patent
Tuurala et al.

(10) Patent No.: US 10,700,363 B2
(45) Date of Patent: Jun. 30, 2020

(54) DEVICE FOR AN ELECTROCHEMICAL CELL

(71) Applicant: Teknologian tutkimuskeskus VTT Oy, Espoo (FI)

(72) Inventors: Saara Tuurala, Espoo (FI); Eero Hurme, Espoo (FI); Anu Vaari, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 111 days.

(21) Appl. No.: 15/756,074

(22) PCT Filed: Aug. 26, 2016

(86) PCT No.: PCT/FI2016/050589
§ 371 (c)(1),
(2) Date: Feb. 28, 2018

(87) PCT Pub. No.: WO2017/037336
PCT Pub. Date: Mar. 9, 2017

(65) Prior Publication Data
US 2018/0241048 A1 Aug. 23, 2018

(30) Foreign Application Priority Data
Aug. 28, 2015 (FI) ...................................... 20155619

(51) Int. Cl.
*H01M 6/32* (2006.01)
*H01M 6/04* (2006.01)
(Continued)

(52) U.S. Cl.
CPC ............. *H01M 6/32* (2013.01); *H01M 6/045* (2013.01); *H01M 6/40* (2013.01); *H01M 6/46* (2013.01);
(Continued)

(58) Field of Classification Search
CPC .................................. H01M 6/32; H01M 6/40
See application file for complete search history.

(56) References Cited

U.S. PATENT DOCUMENTS 6,379,835 B1    4/2002  Kucherovsky et al.
8,758,936 B2    6/2014  Valkiainen et al.
(Continued)

FOREIGN PATENT DOCUMENTS

CN    1780661 A    5/2006
CN    1832777 A    9/2006
(Continued)

*Primary Examiner* — Maria Laios
(74) *Attorney, Agent, or Firm* — Laine IP Oy

(57) ABSTRACT

The present invention relates to a device for an electrochemical cell, comprising a first layer of substrate material having a plurality of first hydrophilic areas of the substrate and at least one hydrophobic area separating said first hydrophilic areas, the first layer of substrate material comprising at least two first electrodes made on at least two first hydrophilic areas; a second layer of substrate material having a plurality of second hydrophilic areas of the substrate and at least one hydrophobic area separating said second hydrophilic areas, the second layer of substrate material comprising at least two second electrodes made on at least two second hydrophilic areas; and one or more electrical conductors connected to at least two of said first electrodes. The first layer of substrate material and the second layer of substrate material are positioned on top of one another such that the at least two first electrodes are aligned with the at least two second electrodes in order to form at least two electrochemical cells for producing voltage when the at least two hydrophilic areas are contacted with an aqueous liquid.

24 Claims, 7 Drawing Sheets

(51) Int. Cl.
  H01M 6/40 (2006.01)
  H01M 6/46 (2006.01)
  *A61N 1/30* (2006.01)
  *A61N 1/04* (2006.01)
  *A61N 1/20* (2006.01)

(52) U.S. Cl.
  CPC ............ *A61N 1/0404* (2013.01); *A61N 1/205* (2013.01); *A61N 1/30* (2013.01)

(56) References Cited

U.S. PATENT DOCUMENTS

| | | |
|---|---|---|
| 2004/0185334 A1 | 9/2004 | Iwamoto |
| 2008/0296154 A1 | 12/2008 | Dilleen et al. |
| 2010/0057147 A1 | 3/2010 | Fassih et al. |
| 2011/0118655 A1 | 5/2011 | Fassih et al. |
| 2011/0271424 A1 | 11/2011 | Revol |
| 2012/0258346 A1* | 10/2012 | Godden .................. H01M 6/32 429/118 |
| 2014/0295244 A1* | 10/2014 | Gaikwad ............... H01M 6/181 429/124 |
| 2017/0018784 A1* | 1/2017 | Yun ........................ H01M 4/06 |

FOREIGN PATENT DOCUMENTS

| | | |
|---|---|---|
| CN | 102593494 A | 7/2012 |
| CN | 104225787 A | 2/2014 |
| CN | 104280444 A | 1/2015 |
| JP | H0554895 A | 3/1993 |
| WO | WO2005079913 A1 | 9/2005 |
| WO | WO2007147947 A2 | 12/2007 |
| WO | WO2011073519 A1 | 6/2011 |
| WO | WO2012172172 A1 | 12/2012 |
| WO | WO2013130145 A3 | 9/2013 |
| WO | WO2014071572 A1 | 5/2014 |
| WO | WO2014178943 A1 | 11/2014 |

* cited by examiner

DEVICE FOR AN ELECTROCHEMICAL CELL

FIELD

The present invention relates to a device for an electrochemical cell. In particular, the present invention relates to an electrochemical cell that is activated when contacted with liquid or moisture. The present invention also relates to uses of the device.

BACKGROUND

Oxidation-reduction or redox reactions take place in electrochemical cells. There are two types of electrochemical cells. Spontaneous reactions occur in galvanic (voltaic) cells; nonspontaneous reactions occur in electrolytic cells. Both types of cells contain electrodes where the oxidation and reduction reactions occur. Oxidation occurs at the electrode termed the anode and reduction occurs at the electrode called the cathode.

The anode of a galvanic cell is negatively charged, since the spontaneous oxidation at the anode is the source of the cell's electrons or negative charge. The cathode of a galvanic cell is its positive terminal.

Devices for electrochemical cells comprising galvanic couples are known in the art e.g. US 2011/0118655 A1 discloses a device for treatment of skin comprising a substrate comprising a plurality of discrete galvanic couples, each galvanic couple comprising a first conductive electrode that is an anode in electronic communication with a second conductive electrode that is a cathode.

Devices with power sources, such as batteries are also known in the art. US 2010/0057147 A1 discloses a device comprising a first electrode, a second electrode and a power delivery unit in electrical communication with the electrodes, the power delivery unit providing a customised dose of electricity to a treatment area.

In both galvanic and electrolytic cells, oxidation takes place at the anode and electrons flow from the anode to the cathode.

WO 2007/147947 discloses a thin film structure comprising a substrate with a thin conductive layer containing an oxidising enzyme mixed with an electron transfer mediator. The thin layer is protected against wetting to allow for its storage in dry conditions and further being sufficiently porous to allow for immediate activation of the oxidizing enzyme when contacted with an aqueous solution.

WO 2013/130145 discloses methods, systems, and devices for implementing a biofuel cell device for extracting energy from a biofuel. In one aspect, a biofuel cell device includes a substrate, an anode including a catalyst to facilitate the conversion of a fuel in a biological fluid in an oxidative process that releases electrons captured at the anode, thereby extracting energy from the fuel substance, a cathode configured on the substrate adjacent to the anode and separated from the anode by a spacing region, and a load electrically coupled to the anode and cathode via electrical interconnects to obtain the extracted energy as electrical energy.

U.S. Pat. No. 8,758,936 discloses a thin film structure, method of producing it and the use thereof. The thin film structure comprises a substrate with a thin conductive layer containing an oxidizing enzyme mixed with an electron transfer mediator. The thin layer is protected against wetting to allow for its storage in dry conditions and further being sufficiently porous to allow for immediate activation of the oxidizing enzyme when contacted with an aqueous solution. The thin film can be used as a cathode in electrochemical fuel cells.

WO 2005/079913 A1 and WO 2014/178943 A1 disclose apparatuses including multiple first reservoirs and multiple second reservoirs joined with a substrate. Selected ones of the first reservoirs include a reducing agent, and first reservoir surfaces of selected ones of the first reservoirs are proximate to a first substrate surface. Selected ones of the second reservoirs include an oxidizing agent, and second reservoir surfaces of selected ones of the second reservoirs are proximate to the first substrate surface. The device is intended for directing the migration of cells and comprises biocompatible electrodes capable of generating a low level electric field or low level micro current when contacted with an electrolytic solution.

SUMMARY OF THE INVENTION

It is an aim of the present invention to provide a simple device for an electrochemical cell.

It is another aim of the invention to provide a method for the production of a device for an electrochemical cell.

It is a further aim of the invention to provide a device for use in the treatment of diseases.

Current devices for the treatment of hyperhidrosis and for promoting microcirculation under skin are less than optimal. They are inconvenient to use, immobilize the patient during treatment, and are costly.

Hyperhidrosis and microcirculation problems are a significant health risk; 2-3% of world's population suffer from excessive sweating, 20% of the world's population is suffering from sweating and 6% of diabetes patients suffer ulceration of the foot due to problems with microcirculation.

The present invention is based on a flexible and customisable device adapted to produce a voltage when a galvanic pair is formed between an anode and a cathode by contact with an aqueous liquid.

The device comprises a flexible substrate upon which anodes and cathodes, i.e. electrodes, are made for example by printing a conducting ink such as, e.g. carbon- or silver-based inks. A layer structure is made by placing at least two layers of substrate on top of each other such that anodes and cathodes on these two layers of substrate are aligned with each other to form a structure for creating electrochemical cells when moisturized. The electrochemical cells, formed by anodes and cathodes and optionally electrolyte between them, can be connected in series or in parallel so that a desired voltage and current is produced by them when the electrochemical cells are contacted with an aqueous liquid.

More specifically, the device according to the present invention is characterised by what is stated in claim 1.

The invention provides several advantages. By means of embodiments, power sources with a simple structure can be manufactured and integrated into a substrate. According to embodiments, it is also possible to print or integrate micro-current-delivering electrical circuits into the substrate and connect to a power source. In such embodiments, electrical circuits can then be used to deliver microcurrent to promote microcirculation under skin, for instance. The device can be single or multi use. The device is also cost efficient and portable. The device is flexible and easy to use.

An embodiment provides a cost-effective method for producing devices.

The device is also easy to store and ship as it can be stored and shipped in an inactive state whereby no voltage is produced. The device is in this inactive state when dry and can be easily activated by contact with liquid. In the inactive state, the terminals of the device do not have a significant potential difference (voltage) and the device will not supply any significant current even when the terminals are short-circuited. This makes the device safe and easy to handle in its inactive state.

Some embodiments the present invention enable home care for end users. It eliminates the need for costly treatments in hospitals and/or by physicians.

Embodiments can also be easily manufactured using current technology and existing printing processes. The components for which are readily available on the market at reasonable cost.

Other features and advantages will become apparent from the following description.

BRIEF DESCRIPTION OF THE DRAWINGS

Next the invention will be examined more closely with the aid of non-limiting embodiments and examples presented in the description below and with reference to the attached drawings, in which.

EMBODIMENTS

The device according to an embodiment can be used to give microcurrent treatment/therapy to skin, and is suitable in applications such as promoting local: 1) blood circulation under skin; 2) wound healing; 3) healing of bruising, anti-aging, skin-whitening; 4) transdermal drug delivery; 5) excessive sweating (hyperhydrosis); 6) pain relief.

One technological feature combines a well-known microcurrent therapy to skin with large area flexible substrates e.g. plastic, fabric, nonwovens, cloth, paperboard etc., integrated with a power source. In one solution a printable, liquid activated power source is integrated into the substrate.

In another solution, microcurrent delivering electrical circuits are printed or integrated into the substrate and connected with a conventional battery, or an external power source, both wireless and wired connections are possible.

Embodiments relate to a device for an electrochemical cell. In an embodiment the device comprises a first layer of substrate material including at least one cathode and at least one anode and a second layer of substrate material including at least one anode and at least one cathode. The first layer and the second layer are located on top of one another and aligned such that the cathodes and anodes in the layers form anode-cathode pairs. The first layer and the second layer thus face each other. The device can also comprise a third layer of substrate material on an outer face of the first layer or the second layer. In an embodiment, a portion of at least one of the first layer and the second layer of substrate material forms hydrophilic separator areas between the cathodes and anodes. At least one electrical conductor is connected to the at least one cathode and anode or at least one anode and cathode. The third layer of substrate material comprises hydrophobic areas forming a liquid flow guidance structure for guiding liquid to the at least one hydrophilic separator area. The device is adapted to produce voltage when the at least two hydrophilic separator areas are contacted with an aqueous liquid. Both the first and second layers contain hydrophobic and hydrophilic parts. The cathodes and anodes are made such as printed on the hydrophilic parts of the substrate material.

Figure 1A:
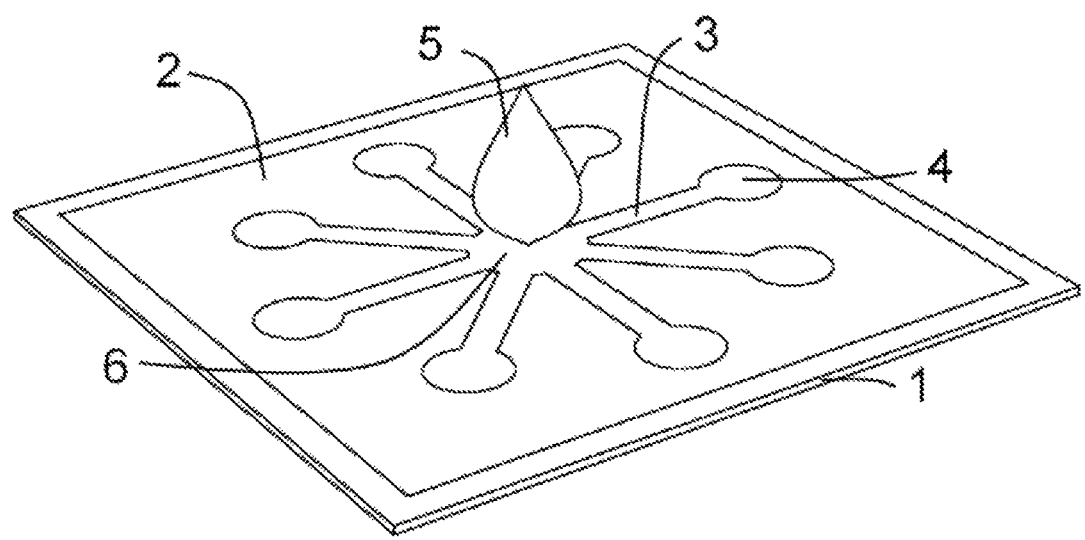
FIG. 1A shows the structure according to one embodiment of the invention.

FIG. 1A illustrates a structure according to an embodiment. A structural layer 2 is formed in a sheet of substrate 1, due to the effect of which liquid can travel in the substrate sheet only along the liquid-flow channels 3 to the detection/reaction areas 4. A sample drop 5 is applied to the intersection 6 of the flow channels. The structural layer 2 extends through the entire depth of the substrate sheet in the thickness direction.

Figure 1B:
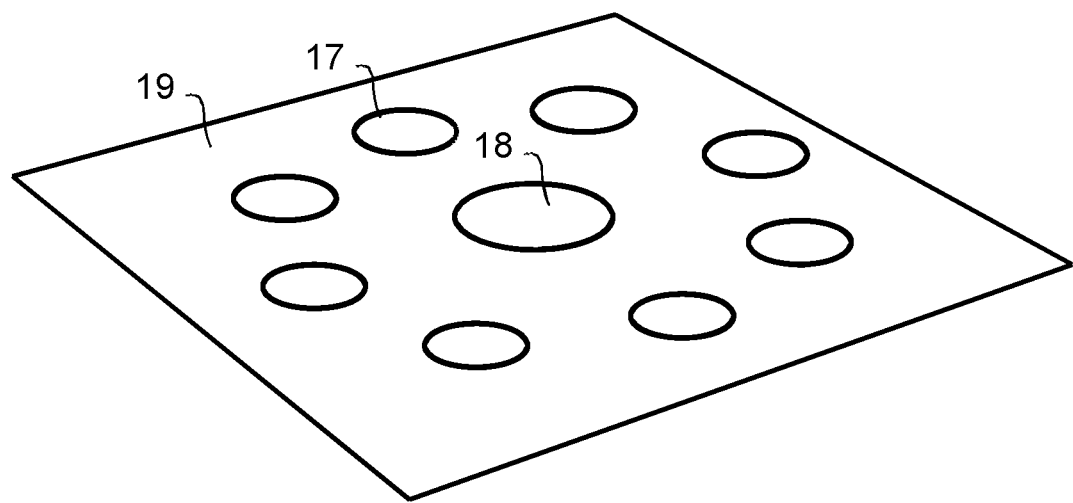
FIG. 1B shows the structure of one layer of the substrate.

FIG. 1B shows the structure of a layer of the substrate 1. The substrate 1 has a hydrophobic area 19, a hydrophilic area 18 and a plurality of electrodes 17 being anodes and/or cathodes. The electrodes 17 are spaced such that when configured with other layers of substrate 1, electrodes 17 overlay or underlie electrodes 17 of the other layers of substrate 1.

Figure 2:
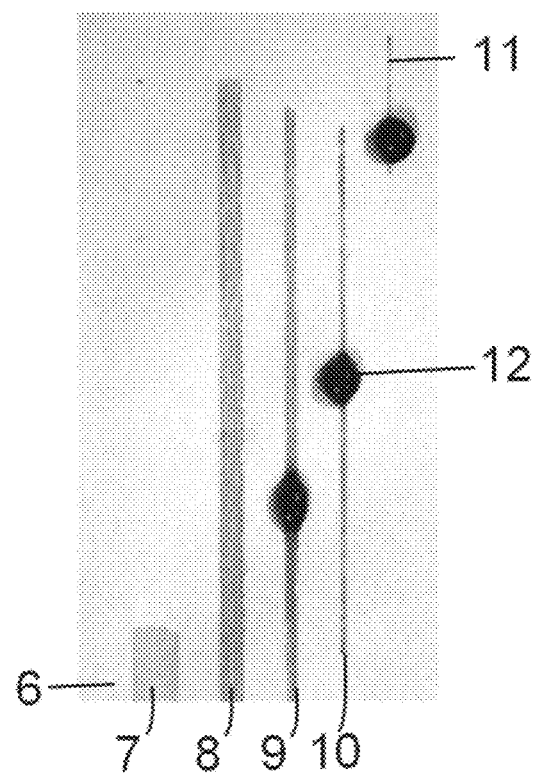
FIG. 2 shows an example of finished structure layers guiding the liquid flow.

FIG. 2 shows an example of liquid-flow guiding structural layers manufactured on paper (50 g/m2) made from Eucalyptus fibres. Due to the effect of the structural layers 16, the liquid can only progress along the liquid channels 7-11. Channel 7 is 4-mm wide and channel 11 is 0.25-mm wide. In the figure, drops of water 12, which have spread by capillary action in the channels, and coloured with foodstuffs colours are applied to the liquid channels. The structural layers 16 guiding the liquid flow are formed in the paper by flexo 15 printing three print layers of a 5 weight-% polystyrene-xylene solution on top of each other. An RK Flexiproof 100 unit was used as the printing device. The printing speed was 60 m/min. The printing cylinder pressure was optimized to achieve the best result. If a single unified printing-solution layer was printed on the rear side of the paper, a single patterned layer on the front side would be sufficient to create patterned liquid channels.

Examples of methods for manufacturing liquid guiding structural layers are explained in more detail in WO 2011/073519 A1, which is incorporated herein by reference.

Figure 3A:
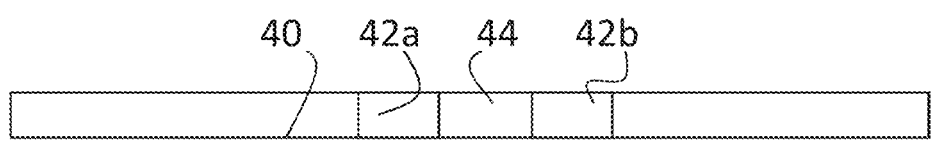
FIG. 3A shows a schematic side cross-section of a structure according to one embodiment of the invention.

FIG. 3A shows schematically the structure according to an embodiment. A first hydrophobic print zone 42a and a second hydrophobic print zone 42b are printed on the substrate 40, between which remains an unprinted hydrophilic sample zone 44. Liquid brought to the sample zone 44 will remain in the zone in question, thanks to the print zones 42a, 42b. The width of a flow channel is typically 30 μm-5 mm, particularly 0.25 mm-4 mm. There can be one or more print layers on top of each other. 1-3 print layers are typically used. By using several layers on top of each other, the polymer can be carried deeper into the substrate to reinforce the liquid-guiding effect of the print structures. A similar effect can also be achieved by increasing the pressure between the printing substrate and the printing cylinder. The polymer concentration, the printing pressure, and the number of printings are preferably selected in such a way that a structure zone extending to the full depth of the substrate is achieved.

Figure 3B:
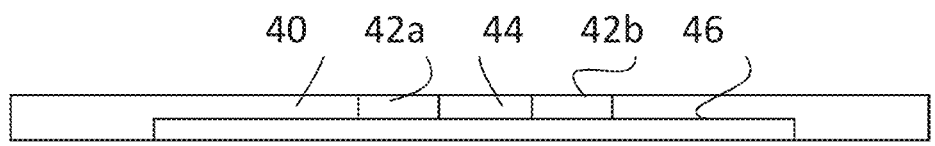
FIG. 3B shows a schematic side cross-section of a structure according to a second embodiment of the invention.

A unified or local barrier layer 46 can also be printed on the rear surface of the substrate, as shown in FIG. 3B. This layer typically extends over the entire width of the sample zone 44 and prevents the liquid from coming through the substrate in its thickness direction. Thus, there is a depth-direction barrier layer 46 in the structure, in addition to the print zones 42a and 42b acting as lateral barrier layers. At the same time, the lateral liquid guiding effect improves and the need for print layers or pressure on the front surface of the substrate is reduced. There is also the advantage that, because the capillary volume decreases, the need for sample substantially decreases. The movement of foreign substances into the sample zone from the base of the substrate (e.g., a table top) is also effectively prevented.

Figure 4:
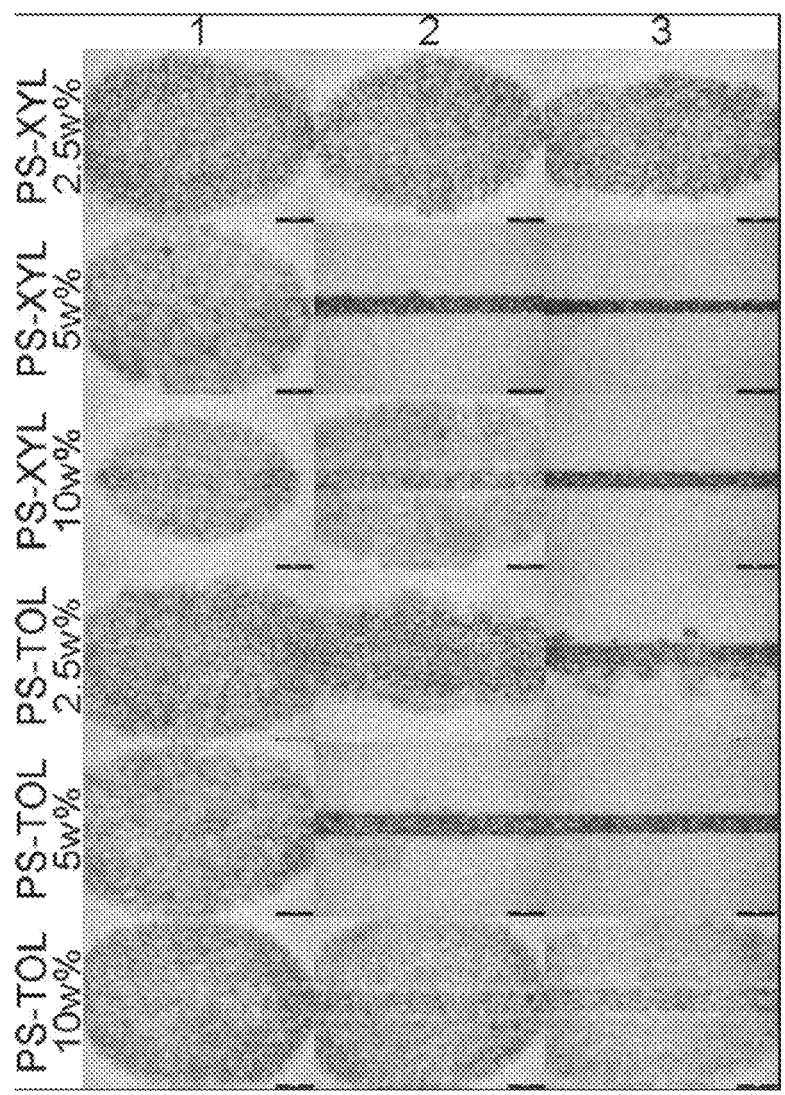
FIG. 4 illustrates the travel of liquid in liquid channels manufactured in different ways.

FIG. 4 shows the spreading of a sample solution in liquid channels made in different ways. Using both a polystyrene-xylene (PS-XYL) solution and a polystyrene-toluene (PS-TOL) solution, the best guiding effect on a sample (foodstuffs-coloured deionized water) was achieved using a polymer concentration of 5 weight-% and using at least two print layers. In all the cases in the figure the width of the solution zone is 1 mm.

Figure 5:
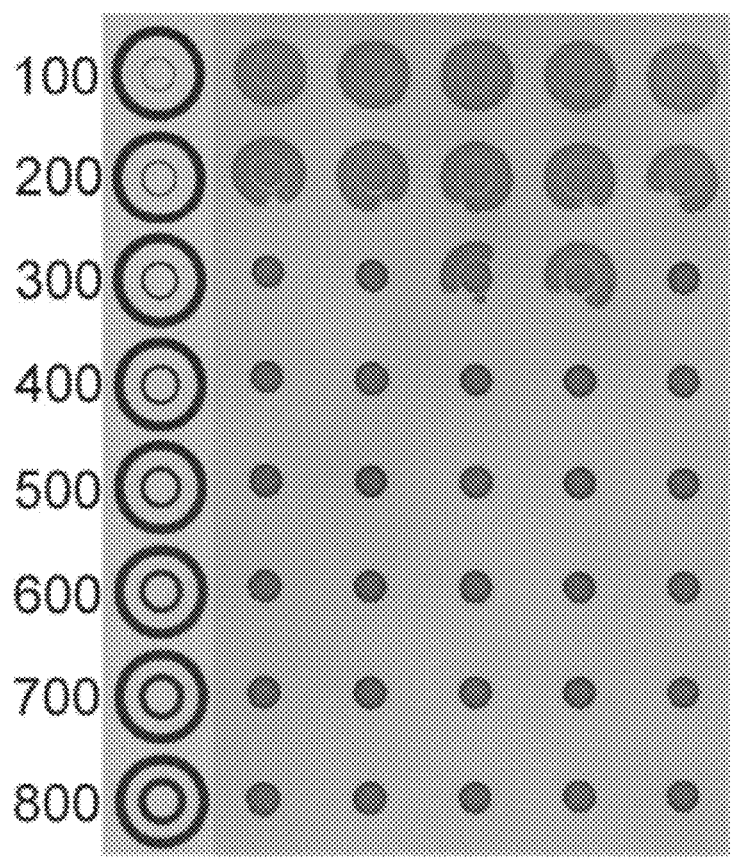
FIG. 5 illustrates the effect of the width of a produced structural zone on its ability to prevent a lateral liquid flow.

FIG. 5 shows the effect of the lateral width of the barrier zone on the capillary travel of a liquid. A 5-weight-% polystyrene-xylene solution was printed on chromatography paper as 100-800-μm rings (inner ring). Inside the ring, 5 μl of coloured deionized water was applied. It was observed that the lateral flow to the barrier zone was entirely prevented using a structural width of about 400 μm.

By optimizing the printing process and the materials, it is possible to achieve structures of even about 100 nm, which are nevertheless sufficiently tight.

For the purposes of the present invention, the term "aqueous liquid" includes, but is not limited to, water, blood, urine, tears, sweat, plasma, saline and mucous.

In an embodiment, the device comprises a first layer of substrate material including at least one cathode and a second layer of substrate material attached on a surface of the first layer of substrate material and including at least one anode, which is aligned with the at least one cathode included in the first layer of substrate material.

In an embodiment, the structure is designed so that at least one hydrophilic separator area is formed between the at least one cathode and the at least one anode.

In a further embodiment, the device also includes a third layer of substrate material positioned on the opposite face of the first layer of substrate material or the second layer of substrate material such that the third layer of substrate material forms a liquid flow guidance structure for guiding liquid to the at least one hydrophilic separator area. The opposite face refers to the face of a first layer or second layer that is oriented away from the second layer or first layer, respectively. The device also comprises at least one electrical conductor connected to at least one cathode or at least one anode. The device is adapted to produce voltage when the at least one hydrophilic separator area is contacted with an aqueous liquid.

The liquid flow guidance structure is manufactured on a substrate sheet for example by flexo or gravure printing, using a printing solution, which changes the properties of the substrate sheet in such a way that the liquid flow is prevented in the area of the printed structural layers. In terms of printing technology, it is compatible with existing printing machines and thus is highly suitable for mass production.

Embodiments also provide the advantage that simple solutions, comprising a polymer and a solvent, or solutions substantially consisting of them, are considerably more economical than, for example, commercial photoresists, which are used in the methods according to the prior art.

The penetration of the printing solution in the depth direction of the substrate sheet is regulated by adjusting the pressure between the printing cylinder and the substrate sheet, and viscosity of the printing solution. By using a suitable printing-cylinder pressure and making a printing solution with a suitable viscosity, the solvent of which evaporates rapidly, the lateral spread of the printing solution is kept small and thus the edge areas of the structures guiding the liquid flow are made sharp. The properties of the printing solution can also be optimized by using a solvent with several different boiling points. The penetration of the printing solution into the substrate sheet can be boosted by printing several printing-solution layers on top of each other, or by applying more printing solution using, for example, screen printing.

If the substrate sheet is so thick, that a printing-solution layer printed on the front side does not penetrate through the entire substrate, either a patterned or a unified printing-solution layer can be printed on the rear surface of the substrate. When the printing-solution layers printed on the front and rear sides meet, a structural layer guiding liquid flow is achieved. If the embodiment is used for the manufacture of liquid-flow channels, a unified printing-solution layer printed on the rear side has the advantage that it simultaneously acts as a protecting layer, which prevents the liquid from escaping through the under surface of the substrate.

The substrate of the device may be selected from a diverse range of materials. In an embodiment the substrate is selected from the group of substrates consisting of textiles, such as, for example cotton, viscose and polyamide, non-woven materials such as, for example, knitted fabrics and netting fabrics, paper and paper board, and technical fabrics such as, for example GORE-TEX®. Each different substrate provides different benefits. By changing the substrate, the time period over which the device is active can be controlled e.g. GORE-TEX® is more breathable than nylon and thus the aqueous liquid closing the electrical circuit evaporates from the device more quickly, reducing the amount of time that the electrical circuit is closed and likewise the amount of time that voltage is produced. In one embodiment the first layer of substrate material, the second layer of substrate material and the third layer of substrate material are made of the same substrate material.

In an embodiment the first layer of substrate material, the second layer of substrate material and the third layer of substrate material are different areas of a single substrate. Thus the first layer, the second layer and the third layer of substrate material are a first area, second area and a third area on the substrate.

In a particular embodiment the at least one electrical conductor is printed on a fourth area of the same single substrate.

In a further embodiment, the first layer of substrate material further includes at least one anode in addition to the at least one cathode and the second layer of substrate material further includes at least one cathode in addition to the at least one anode.

In an embodiment, the device includes a hydrophilic separator area located between each anode-cathode or cathode-anode pair.

In a further embodiment the device contains at least one electrolyte within the at least one hydrophilic separator area.

In a further embodiment the device further comprises connectors for connection to a power source. The power source can for example be connected to the device with leads from the power source to electrodes of the device, i.e. at least one connection lead to an anode of the device and at least one connection lead to a cathode of the device.

In a further embodiment the device comprises a power source, wherein the power source is integrated in the substrate by printing, e.g. by inkjet printing or from the pen of a plotter. If inkjet printing is used, the printing is usually repeated a number of times, typically 10 to 30 times, such as 12 to 20 times. The power source can be printed on the substrate for example by flexo or gravure printing, or by screen printing.

Several fuel sources are possible. In one embodiment the source of energy is a renewable fuel. In a particular embodiment the source of energy comprises a fuel composition comprising at least one compound selected from the group consisting of monosaccharides, such as, for example, glucose, fructose, galactose and ribose, disaccharides such as, for example, lactose, sucrose, maltose, lactulose and cellobiose, alcohols such as, for example, ethanol, methanol, isopropyl alcohol, butanol, tertiary butanol, pentanol and hexanol, lactic acid, uric acid, ascorbic acid and urea. In a further embodiment the source of energy is selected from the group consisting of biofuel cell and half enzymatic cell.

As described above the device comprises at least one cathode and at least one anode. In an embodiment the device comprises a plurality of anodes and a plurality of cathodes, one cathode and one anode forming a galvanic pair. The galvanic pairs are connected in series in one embodiment and in a further embodiment the galvanic pairs are connected in parallel. In a still further embodiment galvanic pairs are connected in a combination of both series and parallel.

In an embodiment the cathode comprises an electrode material, such as an electrically conductive material. In an embodiment the electrode material is selected from the group of carbon, silver, gold, copper, aluminium, palladium, platinum, zinc and mixtures thereof. In an embodiment the anode comprises an electrode material, such as material selected from the group of carbon, silver, gold, copper, aluminium, palladium, platinum, zinc and mixtures thereof.

In an embodiment the anode comprises a catalyst. In an embodiment the catalyst comprises at least one enzyme selected from the group consisting of glucose oxidase, lactate oxidase, urate oxidase and ascorbate oxidase. In a further embodiment the cathode comprises a catalyst, such as at least one enzyme selected from the group consisting of glucose oxidase, monoamine oxidase, cytochrome P450 oxidase, NADPH oxidase, zanthine oxidase, L-gulonolactone, laccase, lysyl oxidase, cytochrome c oxidase, glutathione peroxidase, haloperoxidase, catalase, myeloperoxidase, thyroid peroxidase, vanadium bromoperoxidase and lactperoxidase.

Further embodiments relate to a method of producing a voltage in the device. In order for the device to produce a voltage, the device is activated. In one embodiment a method of producing a voltage in a device of any of the above described embodiments comprises the step of contacting the substrate of the device with an aqueous liquid.

The aqueous liquid may be selected from those liquids that may be considered to be biological fluids. In an embodiment the aqueous liquid is selected from the group consisting of water, urine, tears, saline, blood, plasma, pus, mucous, sweat and mixtures thereof.

The device has a number of applications not only in cosmetics but also in healthcare and wellbeing. The device can be configured such that on folding the substrate, anodes and cathodes are positioned one underlying the other. In such a configuration a device is provided that may be attached by means of a pharmaceutically acceptable adhesive to an area of skin that is to be treated. One embodiment provides the device as described hereinbefore for use in the treatment of diseases.

By activating the device with an aqueous liquid such as the sweat of the person to be treated an electrical voltage is produced and current flows to the skin. This current stimulates the skin enhancing e.g. blood flow. In one embodiment the device is provided for use in the treatment of diseases symptomized by poor blood circulation, such as, for example, preventing pain and diabetic ulcers, peripheral artery disease, alopecia and hair loss. In a further embodiment the device is provided for use in the treatment of wounds, bruises and scars. In a further embodiment the device is provided for use in the treatment of migraine.

Excessive sweating is a condition that can be ameliorated by the passage of electrical current into the afflicted area. Thus, in one embodiment the device is provided for use in the treatment of hyperhidrosis.

The device can also be used for the delivery of drugs by induction of a current over a treatment area. In an embodiment the device is provided for use in the treatment of pain, for example by transdermal drug delivery.

Not only is the device suitable as a tool in drug delivery, but it can also be used in cosmetics. In an embodiment the device is provided for enhancing delivery of cosmetic, well-being and personal care stimulant agents into skin.

A method of producing a device for an electrochemical cell is provided in a further embodiment, said embodiment comprises the steps of printing at least one cathode on an at least one first area of a substrate, printing at least one anode on an at least one second area of the substrate, wherein the printings on the at least one first area and on the at least one second area are separated by an at least one third area of the substrate. In the method the at least one third layer of substrate is provided with an at least one liquid flow guidance structure for guiding liquid. In a further step at least one electrical conductor is provided which is connected to the at least one cathode or the at least one anode, and the at least one anode is juxtaposed with the at least one cathode such that the device is adapted to produce voltage when it is contacted with an aqueous liquid.

In a further embodiment, the juxtaposing of the at least one anode and the at least one cathode is carried out, for example, by folding the substrate so that the at least one anode and at least one cathode underlie and/or overlay an at least one anode and an at least one cathode.

Figure 6A:
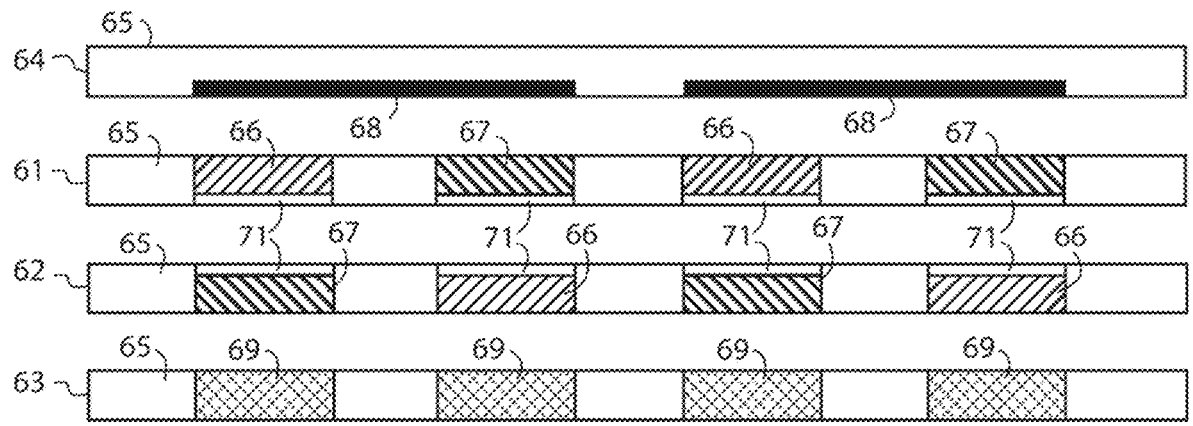
FIG. 6A shows a layered substrate material according to an embodiment of the invention.

FIG. 6A shows a first layer 61 of substrate material 65 and at least one cathode 66 included in the first layer 61. The at least one cathode 66 can be manufactured for example by printing as discussed earlier in this document. In the embodiment of FIG. 6A, the first layer 61 includes also anodes 67. In the embodiment, the first layer 61 also includes a separator layer 71 between the outer surface of the first layer 61 and the inner boundary of the cathode 66 or anode 67 inside the substrate material 65. The outer boundary of the cathode 66 or anode 67, i.e. the upper surface of the cathode 66 or anode 67 of the first layer 61 in the orientation of FIG. 6A, can coincide the surface of the first layer 61 of substrate material 65 or can protrude outward from the surface of the first layer 61 of substrate material 65.

FIG. 6A also shows a second layer 62 of substrate material 65 and at least one anode 67 included in the second layer 62. The at least one anode 67 can be manufactured for example by printing as discussed earlier in this document. In the embodiment of FIG. 6A, the second layer 62 includes also cathodes 66. Just as the first layer 61, also the second layer 62 comprises separator layers 71 between the outer surface of the first layer 61 and the inner boundaries of the cathodes 66 and anodes 67 inside the substrate material 65.

FIG. 6A shows also a third layer 63 of substrate material 65 and at least one hydrophilic collection area 69 formed or left in the substrate material 65. The substrate material 65 is usually hydrophilic itself so that the hydrophilic collection areas 69 can be left untreated or can be provided with an at least one electrolyte in dry form. Instead of, on in addition to, the hydrophilic collection areas 69, the at least one electrolyte can be provided in the separator layers 71 in the first layer 61 or the second layer 62 or in both the first layer 61 and the second layer 62.

Otherwise, the substrate material 65 of the third layer 63 can be made hydrophobic using methods described above, for instance. Then, the hydrophobic areas form a liquid flow guidance structure, which guides the liquid flow by preventing the liquid from being absorbed into the areas the third layer 63 outside of the hydrophilic collection areas 69. In another embodiment, the liquid flow guidance structure comprises liquid channels as described above. In such an embodiment, a hydrophobic pattern is made in the substrate material 65 of the third layer 63 outside of the hydrophilic collection areas 69 to form such liquid channels. Thus, the term collection area refers to the idea that sample fluid is transported by means of the liquid channels to the hydrophilic collection areas 69 from which the liquid is absorbed in between the electrodes 66 and 67 through one of the electrodes in order to activate the current production.

FIG. 6A also shows a fourth layer 64 of substrate material 65 including electrical conductors 68 printed on its surface.

At least one dry electrolyte material can be provided between the anodes 67 and cathodes 66 or in the vicinity of the anodes 67 and cathodes 66 such that electrolyte will be transported to the substrate area between the anodes 67 and cathodes 66 by means of liquid with which the device is contacted. In this case, the device can produce electricity efficiently also when the liquid is pure water as the electrolyte material provides the necessary ions. The electrolyte material can be, for example, a salt, such as ammonium chloride or zinc chloride or other suitable salt or a combination of salts. The device can also be designed to operate without electrolyte materials in the device itself but to be activated by the liquid with which the device is contacted, such as urine or sweat or other salty waters.

Figure 6B:
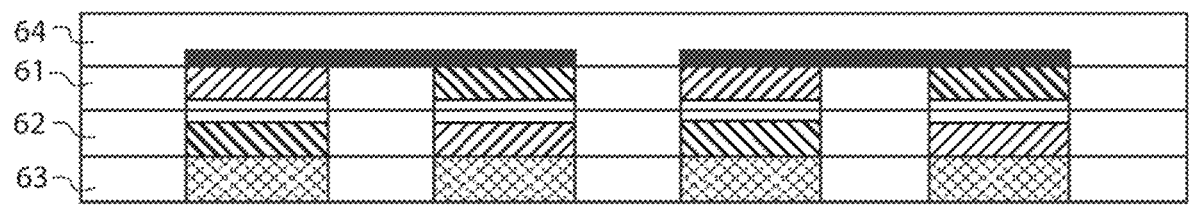
FIG. 6B shows a structure according to an embodiment after stacking of the layers of FIG. 6A.

As shown in FIG. 6B, the layers of FIG. 6A can be connected together to form a device for an electrochemical cell, comprising:

a first layer 61 of substrate material 65 having a plurality of first hydrophilic areas of the substrate and at least one hydrophobic area separating said first hydrophilic areas, the first layer of substrate material comprising at least two first electrodes 66/67 made on at least two first hydrophilic areas;

a second layer 62 of substrate material 65 having a plurality of second hydrophilic areas of the substrate and at least one hydrophobic area separating said second hydrophilic areas, the second layer of substrate material comprising at least two second electrodes 67/66 made on at least two second hydrophilic areas;

one or more electrical conductors 68 connected to at least two of said first electrodes; and wherein the first layer 61 of substrate material 65 and the second layer 62 of substrate material 65 are positioned on top of one another such that the at least two first electrodes 66/67 are aligned with the at least two second electrodes 67/66 in order to form at least two electrochemical cells for producing voltage when the at least two hydrophilic areas are contacted with an aqueous liquid.

In the embodiment of FIGS. 6a and 6b, the first and second hydrophilic areas of the substrate coincide with the electrodes 66/67 and the separator layers 71, and the rest of the substrate material 65 acts as the hydrophobic area separating said hydrophilic areas.

In the embodiment of FIGS. 6a and 6b, the device further comprises a third layer 63 of substrate material 65 comprising hydrophobic areas forming a liquid flow guidance structure (65/69 or liquid channels not shown in the figure) for guiding liquid to the at least one hydrophilic collector area 69 and therefrom to the separator layers 71, and the device is adapted to produce voltage when the separator layers 71 are contacted with an aqueous liquid.

Figure 6C:
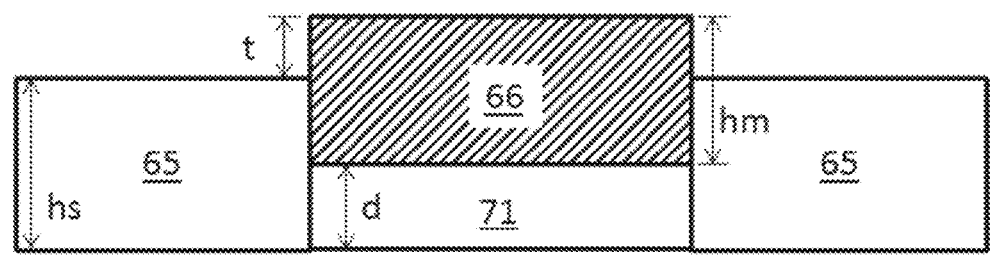
FIG. 6C shows a placement of an electrode in a substrate according to an embodiment.

FIG. 6c shows the positioning of the electrodes (66 and 67) within the substrate material 65 in more detail. In FIG. 6c, the electrode is a cathode 66, but corresponding values and teachings apply also for anodes 67. At the same time, FIG. 6c shows also the positioning of the separator layers 71. FIG. 6c shows also a thickness hs of the substrate material 65, a thickness hm of the electrode 66 and a thickness d of the the separator layer 71. The thickness d is measured between the inner boundary of electrode and the surface of the substrate material 65 to be placed facing the opposite electrode. The thickness hm is measured between the inner boundary of electrode and the outer surface of the electrode. When hm+d>hs, the electrode protrudes outwardly from the surface of the substrate material 65 by a thickness t, which is also shown in FIG. 6c.

In an embodiment, the values for the parameters shown in FIG. 6c are as follows:

hs is 50-1000 µm, such as 100-1000 µm;
hm is 10-1000 µm, such as 50-500 µm;
d is 10-1000 µm, such as 20-100 µm; and
t is 0-1000 µm, such as 10-200 µm.

In another embodiment, t is 5-200 µm, such as 20-50 µm, wherein the outward protrusion of the electrode material facilitates the forming of electrical contact between the electrode 66, 67 and the conductor 68.

In another embodiment, d is 10-200 µm, such as 20-100 µm.

Hence, in an embodiment, the first electrodes 66/67 comprise a layer of electrode material at least partially absorbed within the first layer 61 of substrate material 65 through a first surface of the substrate material 65 (upper surface in FIG. 6a), and the first layer 61 of substrate material 65 comprises a separator layer 71 between the layer of electrode material and a second surface of the substrate material 65 (lower surface in FIG. 6a) opposite to the first surface of the substrate material 65. In other words, the electrode material that is for example printed on the substrate material 65 is at least partially absorbed in the substrate material 65 but not throughout the thickness of the first layer 61. Instead, the electrode material forms a layer acting as an electrode 66/67 on and/or inside the first layer 61, and the rest of the thickness of the first layer 61 acts as the separator layer 71.

In an embodiment, also the second electrodes 67/66 comprise a layer of electrode material at least partially absorbed within the second layer 62 of substrate material 65 through a first surface of the substrate material 65 (lower surface in FIG. 6a), and the second layer 62 of substrate material 65 comprises a separator layer 71 between the layer of electrode material and a second surface of the substrate material 65 (upper surface in FIG. 6a) opposite to the first surface of the substrate material 65. In other words, the electrode material that is for example printed on the substrate material 65 is at least partially absorbed in the substrate material 65 but not throughout the thickness of the second layer 61. Instead, the electrode material forms a layer acting as an electrode 67/66 on and/or inside the second layer 62, and the rest of the thickness of the second layer 62 acts as the separator layer 71.

In an embodiment, the first layer 61 and the second layer 62 both comprise a separator layer 71 so that the distance between the electrodes 66 and 67 in an electrochemical cell is double the thickness of one separator layer 71.

In another embodiment, only one of the first layer 61 and the second layer 62 comprise a separator layer 71.

By means of leaving a separator layer inside the first layer 61 and/or the second layer 62 of substrate material 65, an electrochemical cell can be manufactured without separate membranes or other elements acting as a separator element between the electrodes. Instead, the first layer 61 of substrate material 65 can be placed in direct contact with the second layer 62 of substrate material 65. This simplifies the structure and offers benefits in view of mass production of the electrochemical cells.

In an embodiment, the first layer 61 of substrate material 65 is in direct contact with the second layer 62 of substrate material 65 at least at the locations of the at least two first electrodes and the at least two second electrodes, a portion of the substrate material 65 separating the at least two first electrodes from the at least two second electrodes in the thickness direction of the substrate material 65.

Figure 7:
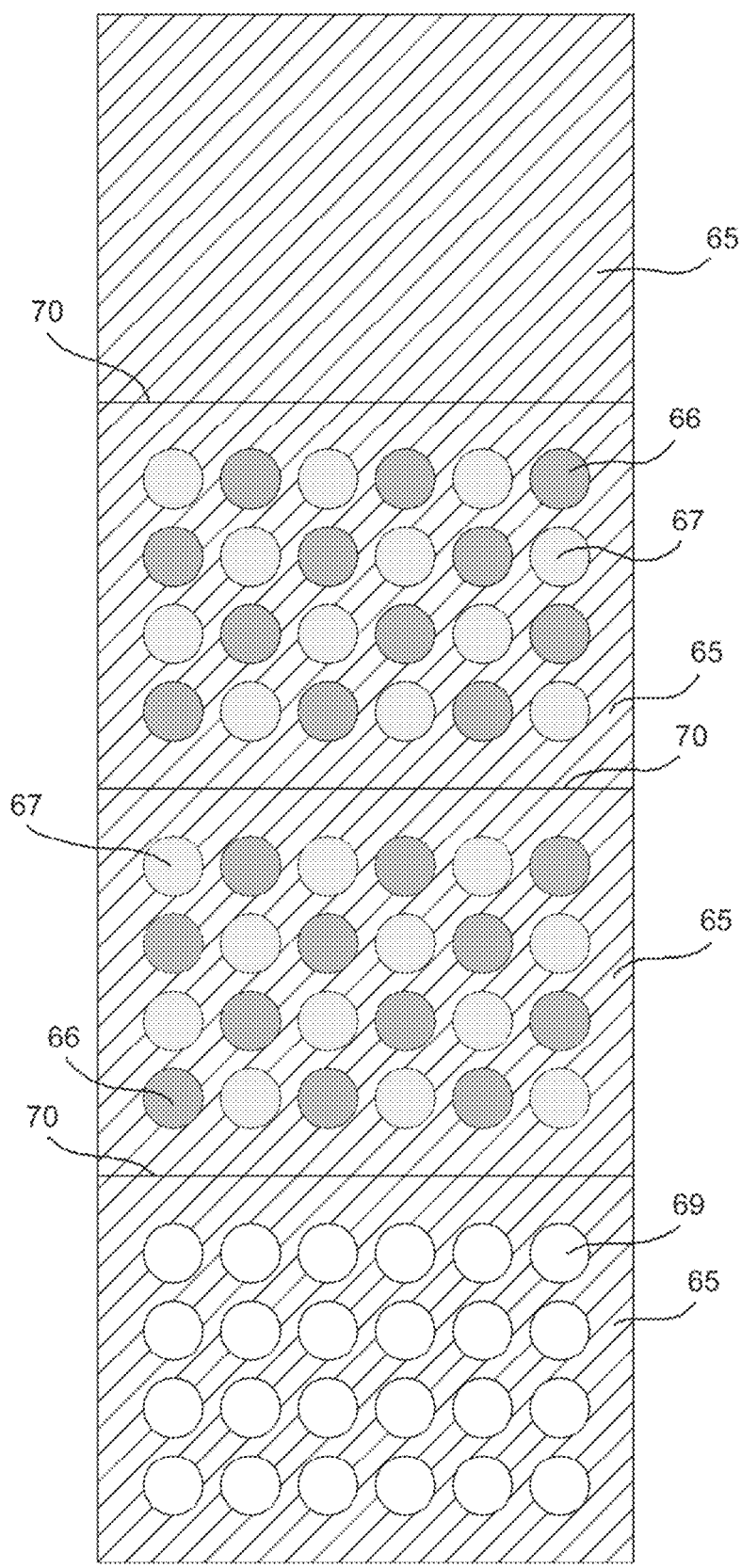
FIG. 7 illustrates a foldable bandage or dressing according to an embodiment of the invention.
Figure 8:
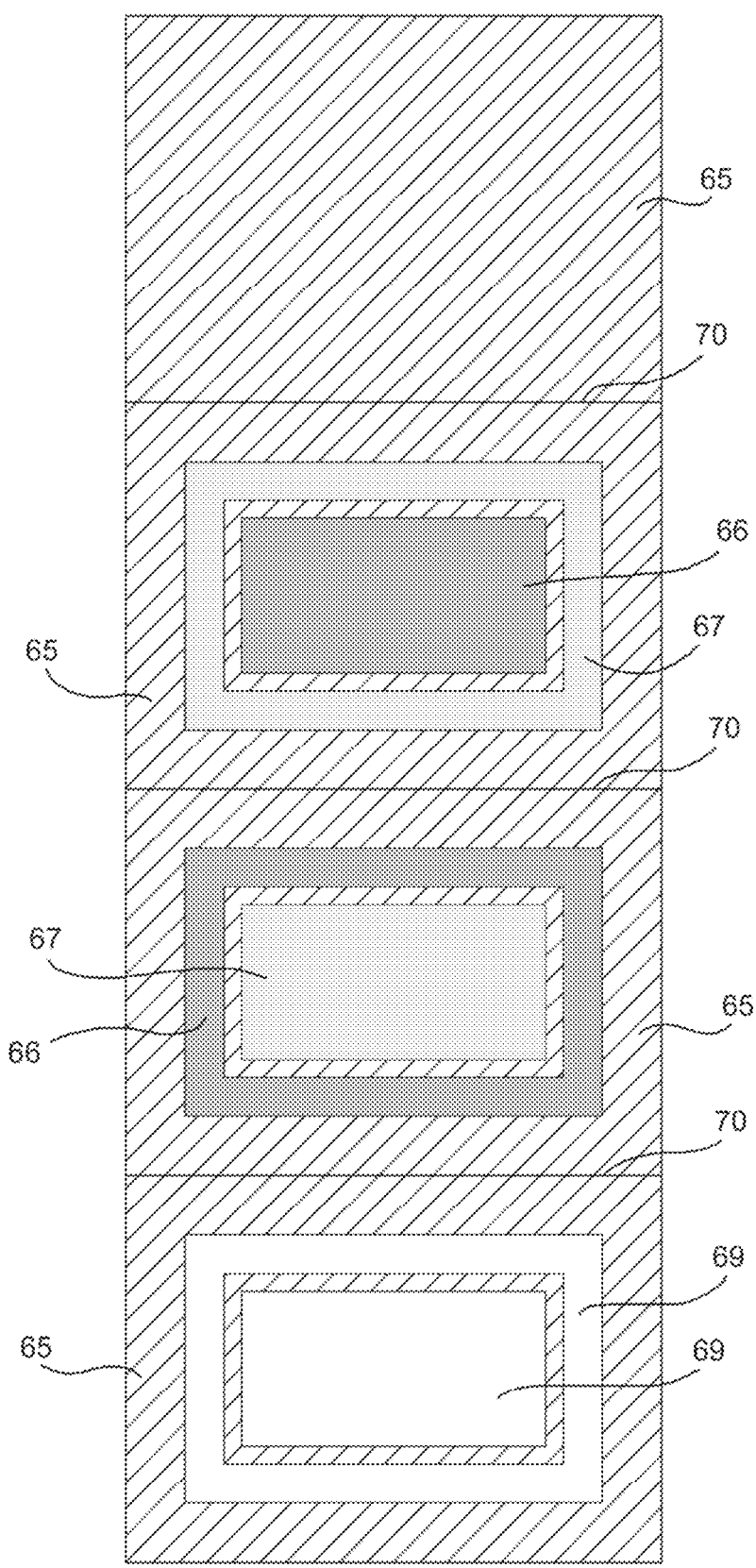
FIG. 8 shows a further example of a foldable bandage or dressing according to an embodiment of the invention.

The substrate material 65 can be the same in each one of the layers 61, 62, 63 and 64. The structure can also be made by printing on a single layer of substrate material 65 and then cutting and juxtaposing the different layers or just folding the structure. The folding is especially practical in embodiments described in FIGS. 7 and 8. In the embodiments of FIGS. 7 and 8, the print patterns are designed so that the differently treated areas of the substrate material 65 are automatically aligned correctly with regard to each other when folded properly along a folding line 70.

By making an outward fold along line 70 between a first portion of substrate material 65 (lowest portion in FIGS. 7 and 8) comprising hydrophilic collector areas 69 and a second portion of substrate material 65 (lowest but one portion in FIGS. 7 and 8) comprising cathodes 66 and anodes 67, the hydrophilic collector areas 69 due to the nature of their positioning on the first portion of substrate material 65 become correctly aligned with regard to the cathodes 66 and anodes 67 of the second portion of substrate material.

The fold provides a layered structure, said structure having a first layer 61 of substrate material 65 comprising cathodes 66 and anodes 67 and a third layer 63 of substrate material 65 comprising hydrophilic collector areas 69. In an embodiment, the third layer 63 is made suitable for contacting a subject, e.g. suitable for contacting the skin, for instance.

By making an inward fold along a second line 70 between the second portion of substrate material 65 comprising cathodes 66 and anodes 67 and a third portion of substrate material 65 (second portion from top in FIGS. 7 and 8) comprising cathodes 66 and anodes 67, the cathodes 66 of the third portion of substrate material 65 become aligned with the anodes 67 of the second portion of substrate material 65. Similarly, the anodes 67 of the third portion of substrate material 65 become aligned with the cathodes 66 of the second portion of substrate material 65.

This fold provides a second layer 62 of substrate material 65 comprising cathodes 66 and anode 67 to the layered structure.

In a further embodiment, the substrate material comprises also a fourth portion (top most portion in FIGS. 7 and 8). By making a further fold along a line 70 between the third portion of substrate material 65 comprising cathodes 66 and anodes 67 and a fourth portion of substrate material is provided according to an embodiment. The fourth portion can be used to create contacts between the galvanic pair, i.e. between cathodes 66 and anodes 67 depending on the type of connection (serial or parallel). The layer containing conductors can be easily configured such that the desired galvanic pairs are connected to each other.

INDUSTRIAL APPLICABILITY

Products according to embodiments are suitable for use in the production of wearable flexible thin printed batteries.

There is an increasing demand for new functionalities e.g. for textiles and textile based products. Wearable and flexible products as well as devices connected to the "Internet-of-Things" potentially offer a large market for thin printed batteries going forward; big enough to make the whole thin battery opportunity much more worth pursuing than ever before (Nanomarkets, 2013).

Current devices for the treatment of both wounded and intact skin areas basically work. However, this invention describes a larger area, on demand activable bandages for active, on demand transdermal compound delivery through the skin, and healing under the skin.

| | Reference Signs List |
|---|---|
| 1 | substrate sheet |
| 2 | structural layer |
| 3 | liquid-flow channels |
| 4 | detection/reaction areas |
| 5 | sample drop |
| 6 | intersection |
| 7-11 | liquid channels |
| 12 | drop of water |
| 16 | structural layer |
| 17 | electrodes |
| 18 | hydrophilic area |
| 19 | hydrophobic area |
| 40 | substrate |
| 42a | first hydrophobic print zone |
| 42b | second hydrophobic print zone |
| 44 | hydrophilic sample zone |
| 46 | barrier layer |
| 61 | first layer |
| 62 | second layer |
| 63 | third layer |
| 64 | fourth layer |
| 65 | substrate material |
| 66 | cathode |

-continued

| | Reference Signs List |
|---|---|
| 67 | anode |
| 68 | electrical conductor |
| 69 | hydrophilic collection area |
| 71 | separator layer |

CITATION LIST

1. US 2011/0118655 A1
2. US 2010/057147 A1
3. WO 2011/073519
4. WO 2013/130145
5. U.S. Pat. No. 8,758,936
6. WO 2005/079913
7. WO 2014/178943

The invention claimed is:

1. A device for an electrochemical cell, comprising:
a first layer of substrate material having a plurality of first hydrophilic areas and at least one hydrophobic area separating said first hydrophilic areas, the first layer of substrate material comprising at least two first electrodes made on at least two of the first hydrophilic areas, wherein the at least two first electrodes comprise a layer of electrode material at least partially absorbed within the first layer of substrate material through a first surface of the substrate material, and wherein the first layer of substrate material comprises a separator layer between each of the at least two first electrodes and a second surface of the substrate material, the second surface opposite to the first surface of the substrate material;
a second layer of substrate material having a plurality of second hydrophilic areas and at least one hydrophobic area separating said second hydrophilic areas, the second layer of substrate material comprising at least two second electrodes made on at least two second hydrophilic areas; and
one or more electrical conductors connected to at least two of said first electrodes; and
wherein the first layer of substrate material and the second layer of substrate material are positioned on top of one another such that the at least two first electrodes are aligned with the at least two second electrodes to form at least two electrochemical cells for producing voltage when the separator layers are contacted with an aqueous liquid; and
wherein the substrate comprises a porous substrate selected from the group consisting of a textile, a non-woven material, and a technical fabric.

2. The device according to claim 1, wherein the first layer of substrate material and the second layer of substrate material comprise different first and second areas of a single substrate.

3. The device according to claim 2, further comprising a fourth layer of substrate material positioned beneath the first or second layers of substrate material, wherein the fourth layer of substrate material is optionally a fourth area of the same single substrate which comprises the first and second areas.

4. The device according to claim 1, wherein the first and second hydrophilic areas of the first layer of substrate material and the second layer of substrate material face each other and the at least two first electrodes and the at least two second electrodes are aligned to form the at least two electrochemical cells.

5. The device according to claim 1, wherein the at least two second electrodes comprise a layer of electrode material at least partially absorbed within the second layer of substrate material through a first surface of the second layer of substrate material, and wherein the second layer of substrate material further comprises a separator area between the layer of electrode material and a second surface of the second layer of substrate material opposite to the first surface of the second layer of substrate material.

6. The device according to claim 1, wherein the separator layers have a thickness d of 10-200 μm.

7. The device according to claim 1, further comprising a third layer of substrate material positioned on top of the first or second layer of substrate material, wherein the first, second, and third layers are formed from a single substrate and comprise first, second, and third areas of the single substrate, and wherein the third layer having one or more third hydrophilic areas and at least one third hydrophobic area, wherein the one or more third hydrophilic areas are aligned with one or more of the first and second hydrophilic areas.

8. The device according to claim 7, wherein the third layer of substrate defines a liquid flow guidance structure comprised of the one or more third hydrophilic areas and the at least one third hydrophobic area.

9. The device according to claim 1, wherein the at least two first electrodes comprise at least one anode and at least one cathode and the at least two second electrodes comprise at least one anode and at least one cathode.

10. The device according to claim 1, wherein the at least two first electrodes comprise first anodes and first cathodes and the at least two second electrodes comprise respective second cathodes and second anodes, and wherein the first cathodes and electrodes are aligned with the second anodes and second cathodes, respectively, to form the at least two electrochemical cells.

11. The device according to claim 1, wherein galvanic cells are formed between the at least two first electrodes and the at least two second electrodes when the device is contacted with an aqueous liquid.

12. The device according to claim 11, wherein the galvanic cells are connected in series or in parallel.

13. The device according to claim 11, wherein at least some of the galvanic cells are connected in series and at least some of the galvanic cells are connected in parallel.

14. The device according to claim 1, wherein the first layer of substrate material is in direct contact with the second layer of substrate material at least at the locations of the at least two first electrodes and the at least two second electrodes, and wherein a portion of the substrate material separates the at least two first electrodes from the at least two second electrodes in a thickness direction of the substrate material in each of the first and second layers.

15. The device according to claim 1, having an inactive state, wherein the device produces substantially no voltage and an active state, wherein the device produces voltage.

16. The device according to any claim 15, wherein the device changes from the inactive state to the active state when contacted with the aqueous liquid.

17. The device according to claim 1, wherein the device is inactive when the aqueous liquid is absent.

18. The device according to claim 1, wherein the separator layers have a thickness d 20-100 μm.

19. The device according to claim 1, wherein the substrate is selected from the group consisting of cotton, viscose, polyamide, knitted fabrics, netting fabrics, paper, paper board, and expanded polytetrafluoroethylene.

20. A method of producing a voltage in a device comprising the step of contacting the substrate of the device with an aqueous liquid, and wherein the device comprises:
   a first layer of substrate material having a plurality of first hydrophilic areas and at least one hydrophobic area separating said first hydrophilic areas, the first layer of substrate material comprising at least two first electrodes made on at least two first hydrophilic areas, wherein the at least two first electrodes comprise a layer of electrode material at least partially absorbed within the first layer of substrate material through a first surface of the substrate material, and wherein the first layer of substrate material comprises a separator layer between each of the at least two first electrodes and a second surface of the substrate material, the second surface opposite to the first surface of the substrate material;
   a second layer of substrate material having a plurality of second hydrophilic areas and at least one hydrophobic area separating said second hydrophilic areas, the second layer of substrate material comprising at least two second electrodes made on at least two second hydrophilic areas; and
   one or more electrical conductors connected to at least two of said first electrodes;
   wherein the first layer of substrate material and the second layer of substrate material are positioned on top of one another such that the at least two first electrodes are aligned with the at least two second electrodes to form at least two electrochemical cells for producing voltage when the separator layers are contacted with an aqueous liquid; and
   wherein the substrate comprises a porous substrate selected from the group consisting of a textile, a non-woven material, and a technical fabric.

21. The method of claim 20, wherein the aqueous liquid is selected from the group consisting of water, urine, tears, saline, blood, plasma, pus, mucous, sweat and mixtures thereof.

22. The method according to claim 20, wherein the substrate is selected from the group consisting of cotton, viscose, polyamide, knitted fabrics, netting fabrics, and expanded polytetrafluoroethylene.

23. A method of producing a device for an electrochemical cell, comprising the steps of:
   providing a substrate material having a plurality of hydrophilic areas of the substrate and at least one hydrophobic area separating said hydrophilic areas;
   printing electrodes on the plurality of hydrophilic areas of the substrate material;
   folding the substrate material to form:
      a first layer of substrate material having a plurality of first hydrophilic areas and at least one hydrophobic area separating said first hydrophilic areas, the first layer of substrate material comprising at least two first electrodes made on at least two of the first hydrophilic areas; and
      a second layer of substrate material having a plurality of second hydrophilic areas and at least one hydrophobic area separating said second hydrophilic areas, the second layer of substrate material comprising at least two second electrodes made on at least two of the second hydrophilic areas;
   wherein the first layer of substrate material and the second layer of substrate material are positioned on top of one another such that the at least two first electrodes are aligned with the at least two second electrodes in order to form at least two electrochemical cells for producing voltage when the device is contacted with an aqueous liquid;
   wherein the substrate comprises a porous substrate selected from the group consisting of a textile, a non-woven material, and a technical fabric; and
   connecting one or more electrical conductors to at least two of said first electrodes.

24. The method according to claim 23, wherein the substrate is selected from the group consisting of cotton, viscose, polyamide, knitted fabrics, netting fabrics, and expanded polytetrafluoroethylene.

* * * * *